United States Patent [19]
Armini et al.

[11] Patent Number: 6,059,714
[45] Date of Patent: May 9, 2000

[54] RADIOACTIVE MEDICAL DEVICES

[75] Inventors: Anthony J. Armini, Manchester-by-the-Sea; Stephen N. Bunker, Wakefield, both of Mass.

[73] Assignee: Implant Sciences Corporation, Wakefield, Mass.

[21] Appl. No.: 09/277,305

[22] Filed: Mar. 26, 1999

[51] Int. Cl.$^7$ ........................................ A61N 5/00
[52] U.S. Cl. ................................................. 600/3
[58] Field of Search ........................ 600/3; 427/527, 427/38; 356/312, 85

[56] References Cited

U.S. PATENT DOCUMENTS

| | | | |
|---|---|---|---|
| 3,883,248 | 5/1975 | Rakhovsky et al. | 356/85 |
| 4,800,100 | 1/1989 | Herbots et al. | 427/38 |
| 5,059,166 | 10/1991 | Fischell et al. | 600/3 |
| 5,342,283 | 8/1994 | Good | 600/8 |
| 5,376,617 | 12/1994 | Kumagae et al. | 503/221 |
| 5,871,437 | 2/1999 | Alt | 600/3 |

OTHER PUBLICATIONS

Fishcell et al., "Low–Dose β–Particle Emission From 'Stent' Wire Results in Completw, Localized Inhibition of Smooth Muscle Cell Proliferation," *Circulation*, 90:2956–2963 (1994).

Laird, J. R. et al., "Inhibition of Neointimal Proliferation with Low–Dose Irradiation From a β–Particle–Emitting Stent," *Circulation*, 93:529–536 (1996).

Teirstein, P. S. et al., "Catheter–Based Radiotherapy To Inhibit Restenosis After Coronary Stenting", *New England Journal of Medicine*, 336:1697–1703 (1997).

Wiedermann, J. G. et al., "Intracoronary Irradiation Markedly Recduces Restenosis After Balloon Angioplasty in a Porcine Model," *J. Am. Coll. Cardiol.*, 23:1491–1498 (1994).

*Primary Examiner*—Max Hindenburg
*Assistant Examiner*—Brian Szmal
*Attorney, Agent, or Firm*—Foley, Hoag & Eliot, LLP; David P. Halstead

[57] ABSTRACT

An implantable medical device according to the present invention comprises a body, such as a stent or a wire, having a radioisotope or non-radioactive precursor isotope associated with the body. The isotope preferably is disposed on the body using an efficient deposition method, such as an effusion cell. The method reduces the waste of costly isotopes and reduces the buildup of hazardous material in the apparatus. A metal layer may be deposited simultaneously with or subsequent to deposition of the isotope to encapsulate the radioactive isotope.

25 Claims, 3 Drawing Sheets

RADIOACTIVE MEDICAL DEVICES

TECHNICAL FIELD

This invention relates to the field of radioactive medical devices, in particular, to radioactive medical devices used to restore patency to coronary arteries.

BACKGROUND OF THE INVENTION

Radioactive devices have found a host of uses in modern medicine, especially for treating cancerous growths and restenosis. Certain non-malignant growths have been shown to be responsive to radiation treatment, and may be amenable to treatment with an implantable radioactive medical device.

After balloon angioplasty, a metal tubular scaffold structure called a stent may be permanently implanted to physically hold open the repaired coronary artery. Unfortunately, up to 30% of such procedures result in narrowing or reclosure (restenosis) of the artery within six months to one year. One solution to the problem is to provide acute local, postoperative radiation treatment of the site using a catheter tipped with iridium-192 radioisotope. In this method the iridium-192-tipped catheter is placed at the arterial site for thirty to forty minutes after stent deployment and then retracted. This type of acute high dose treatment using gamma radiation has been found to substantially reduce the rate of subsequent restenosis, as noted in Wiedermann, J. G. et al., "Intracoronary Irradiation Markedly Reduces Restenosis After Balloon Angioplasty in a Porcine Model", 23 J. Am. Coll. Cardiol., 1491–1498 (May 1994) and Teirstein, P. S. et al., "Catheter-Based Radiotherapy to Inhibit Restenosis After Coronary Stenting", 336 New England Journal of Medicine, 1697–1703 (Jun. 12, 1997).

This method of irradiating the patient suffers from the hazards associated with the required high radiation intensity. In addition to the surgeon, an oncologist and a radiation physicist are typically required for the procedure. A heavily shielded lead vault is needed to separate the patient from the operating room personnel, and the task of safely inserting the catheter containing the intense source, which is on the order of about 0.75 Curies, is particularly difficult. If irregularities occur in the procedure, the surgeon has relatively little time to respond, and therefore emergency procedures must be well-rehearsed. This method, while possible in a research environment, may not be practical for many clinics and community-based hospitals.

An alternate method of addressing the restenosis problem is to embed within the structural material of the stent itself a radioactive material, such as described by Fischell et al. in U.S. Pat. No. 5,059,166 (the '166 patent) and in U.S. Pat. No. 5,176,617 (the '617 patent). The '166 and '617 patents also describe methods of electroplating a radioactive material on the structural material of the stent. These methods have certain drawbacks. Placement of radioactive material within the structural material of the stent can present fabrication difficulties with respect to radiation exposure of workers during the manufacturing process. The electroplating process may result in poor adhesion of the radioactive material, which could delaminate during insertion or stent expansion. Although electroplating is an inexpensive technique, electroplating does not work well on devices made of stainless steel or nitinol, and there are many desirable radioactive elements that cannot readily be electroplated. Also, electroplating and many other types of coating technologies, for example sputtering, cathodic arc, or magnetron sources as taught by Good, et al. in U.S. Pat. No. 5,342,283, generally require a relatively large quantity of specially fabricated and prepared feedstock material to be successfully employed. These technologies are ineffective when only a few milligrams of feedstock are available.

Another method mentioned by Fischell and investigated by Laird, J. R. et al., in "Inhibition of Neointimal Proliferation with a Beta Particle Emitting Stent", Circulation 1996; 93:529–536 (the 'Laird article'), is to impregnate titanium stents with up to thirty atom percent of stable phosphorous and subsequently activate the entire stent in a nuclear reactor to form the radioisotope $^{31}$P within the titanium structural material. One of the disadvantages of the Laird method is that the massive quantity (30 atom %) of phosphorous required to achieve even 0.15 microcuries from $^{31}$P may severely alter the structural strength of the stent itself.

In the preferred embodiment of the '166 and '617 patents, the structural material in the body of the stent is alloyed with a non-radioactive precursor element and then subsequently activated in a nuclear reactor to generate the radioactive isotope. However, if the body of the stent or any similar implantable medical device (including, for example, cancer irradiation needles, shunts, vascular grafts, bone screws, and femoral stem implants) contains significant quantities of iron and/or chromium, as is true of stainless steel, for example, then neutron activation produces long-lived radioisotopes which emit a substantial quantity of gamma rays. The emission of these gamma rays is not desirable in a permanent implant because of the resulting high total body dose of radiation.

Another method for embedding the desired radioisotopes in the body of the stent is known as ion implantation. This has been described by Janicki et al. ("Production and Quality Assessment of Beta Emitting $^{32}$P Stents for Applications in Coronary Angioplasty", 42nd Annual Meeting of the Canadian College of Physicist in Medicine, Jun. 20–22, 1996, University of British Columbia, Vancouver, Canada.) and by Fischell et al. (Low-Dose, β-Particle Emission From 'Stent' Wire Results in Complete, Localized Inhibition of Smooth Muscle Cell Proliferation" Circulation 90 :1994) specifically for $^{32}$P-containing stents. A radioactive ion source for $^{32}$P is described in co-pending application U.S. Ser. No. 08/887,504, which is hereby incorporated by reference.

Ion implantation consists of ionizing individual atoms of the radioactive species, accelerating the charged atoms through a high voltage, and directing the resultant beam onto the surface of a device. The high velocity of the accelerated atoms causes the impinging atoms to be embedded below the surface of the device and thus to become incorporated within the body of the device. The ion implantation process may utilize a magnetic mass filter device which separates the atoms of the desired radioisotope from the large family of isotopes that may be produced when the atoms are first ionized. Since only a relatively small quantity of radioactive atoms are required to produce the desired intensity of radioactivity, it is possible to avoid the problem encountered in the Laird method, wherein a high concentration of alloying material may modify the structural strength of the device material.

While ion implantation has been successfully demonstrated to embed radioactive $^{32}$P within a stent, ion implantation of other radioactive isotope species is more difficult. For example, the radioactive isotope $^{103}$Pd requires as much as 30 times the activity level of $^{32}$P for a similar therapeutic effect, thus making the task of ion-implanting $^{103}$Pd much more difficult. In particular, the radioactive isotope feedstock must be utilized much more efficiently than usual (typically between 0.1 and 0.5%) in order to avoid accumulating large quantities of radioactive palladium waste throughout the ion implanter. Radioactive isotopes are expensive, and the waste of most of the radioactive material is both costly and hazardous because of the accumulated radioactive contamination which escapes being ion implanted into the medical device. In addition, there is also an increased risk of radiation dose to personnel who would have to periodically maintain the inefficient, radioactive evaporation apparatus.

Although numerous techniques have been devised to coat or implant radioactive material onto medical devices, none of these techniques transfer the radioactive material with a high efficiency. As a result, these techniques are inadequate, particularly when only a few milligrams of source material are available.

SUMMARY OF THE INVENTION

The invention comprises methods for manufacturing radioactive medical devices which comprise a body having disposed thereon a coating of one or more radioactive isotopes or non-radioactive precursor isotopes, and apparatus for carrying out the methods. This invention further comprises implantable medical devices manufactured by these methods. The methods and apparatus allow radioactive material or non-radioactive precursor material to be deposited on the body of a medical device with high efficiency, and further confer the ability to recycle the radioactive or precursor material that is not constructively deposited during the process.

In one embodiment, the method comprises disposing a radioisotope or non-radioactive precursor isotope on a body under conditions sufficient for the isotope to become associated with the body, e.g., by vapor deposition. The radioisotope or non-radioactive precursor isotope may then be encapsulated by a metal coating either simultaneous with or subsequent to disposing the radioisotope or non-radioactive precursor isotope on the body. Optionally, the metal coating may comprise a biocompatible material, or a biocompatible material may be disposed onto the device following encapsulation by the metal coating. In certain embodiments, an adhesion layer may be deposited between the isotope and the body.

A body useful in the medical device of the present invention comprises any structure, device, or article having characteristics such as stability, resiliency, structure, and shape suitable for use as an implantable radioactive medical device. The body may comprise, for example, a stent, seeds, wire, or other articles suitable for implantation in a patient to deliver a localized dose of radiation. The body may comprise a metal, metal alloy, or ceramic. For example, a titanium alloy, titanium-vanadium-aluminum alloy, rhodium, vanadium, palladium, rhenium, aluminum, nickel, nitinol (NiTi), stainless steel, and alloys of stainless steel such as type 404 steel may be used. Preferred metals and metal alloys comprise stainless steel, rhodium, palladium, titanium, Ti-6-4 (90% titanium, 6% vanadium, and 4% aluminum), and nitinol (50% nickel and 50% titanium). Ceramics useful in the present invention may comprise, for example, quartz (silicon dioxide), alumina (aluminum oxide), titania (titanium dioxide), and zirconia (zirconium oxide).

Figure 1:
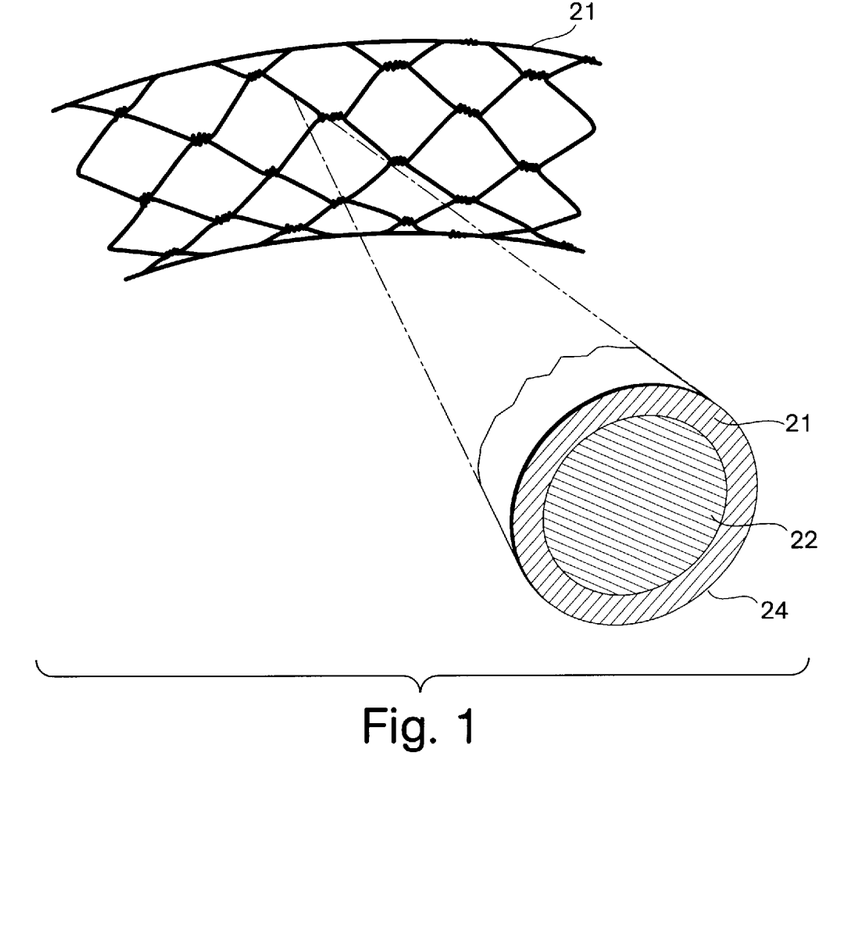
FIG. 1 illustrates a side-view and a cross-section of a single wire of a tubular mesh stent according to the present invention.

In a currently preferred embodiment, the body comprises a stent, said stent being a medical device that can be placed within the lumen of a tubular structure to provide support during or after anastomosis or catheterization, or to assure patency of an intact but contracted lumen. FIG. 1 shows an example of a stent which can be used in coronary arteries. In this embodiment, the shape of the body may be a tubular mesh shape, a helical coil shape, or any of a variety of other shapes suitable for a stent.

In a preferred embodiment, the present method comprises depositing a radioactive, costly, or otherwise precious or hazardous material in an efficient manner by the judicious selection of the isotope source. The isotope source preferably provides the radioisotope or non-radioactive precursor isotope as a focused stream of vapor. This may be accomplished, for example, by heating the isotope using a device called an effusion cell to vaporize the isotope. An effusion cell comprises a thermally heatable enclosed volume, within which the radioactive isotope or non-radioactive precursor isotope is placed, together with a small diameter aperture through which the resulting vapor is expelled. An effusion cell differs from an ordinary evaporator in that most or, preferably, all surfaces within the enclosed volume are heated to a temperature sufficient to sublimate the evaporant. The vapor is expelled into a vacuum chamber, and thus the interior of the effusion cell is also at vacuum pressure. The effusion cell provides a flow of vapor in the form of condensable gas which may be utilized to coat a surface. In preferred embodiments, the layer of radioisotope or non-radioactive precursor isotope is less than about 250 Å thick, even more preferably between about 50 Å and about 100 Å.

Stable, non-radioactive precursor isotopes useful in the invention may be any isotope which, upon thermal neutron activation, generates a radioactive isotope having the desired emission profile. Exemplary precursor isotopes having this property include, for example, ytterbium-168, barium-130, phosphorus-31, palladium-102, yttrium-89, rhenium-185, and rhenium-187. Mixtures or combinations of more than one precursor isotope may be used.

Radioisotopes useful in the present invention may be any therapeutically or prophylactically effective radioactive material. Preferred radioisotopes comprise, for example, phosphorus-32, iodine-125, palladium-103, yttrium-90, cesium-131, and ytterbium-169. Mixtures or combinations of more than one type of radioactive isotope may be used in the device.

When more than one type of radioactive isotope or non-radioactive precursor isotope is deposited on the medical device, separate effusion cells whose temperatures, and thus evaporation rates, are individually controlled, may be employed for each isotope.

The amount of radioisotope deposited on the body may be monitored by substantially simultaneously detecting the amount of radioactivity emitted by the body during deposition of the radioisotope.

In embodiments wherein a non-radioactive precursor isotope is deposited, the isotope is activated by exposing the device to a source of thermal neutrons to generate a radioactive isotope having the desired emission profile. The body and any coatings disposed thereon preferably will not include materials, such as stainless steel, chromium, or nickel, which may generate undesirable radioisotopes when exposed to a source of thermal neutrons, unless the duration of the exposure is limited.

An additional metal layer also may be deposited onto the body to encapsulate the radioactive material. Examples of such metals comprise, but are not limited to, titanium, gold, tantalum, carbon, titanium-aluminum-vanadium alloy, stainless steel, cobalt-chrome alloy, cobalt-chrome-molybdenum alloy, rhodium, lead, silicon, copper, platinum, and palladium. Preferred materials comprise titanium, titanium alloy, gold, copper, tantalum, stainless steel, cobalt-chrome alloy, platinum, and palladium. The metal layer may be deposited simultaneously with or subsequent to the deposition of the radioisotope or non-radioactive precursor isotope. Alternately, the radioisotope or non-radioactive precursor isotope may be ion-implanted into the encapsulated metal layer. The metal layer is produced from a source separate from the isotope source. This separate source may employ any of a variety of well known coating methods, such as thermal boat evaporation, electron beam evaporation, sputtering, or another effusion cell. When the metal layer is deposited after deposition of the isotope, the metal layer may be deposited in a separate step or in a separate device from the isotope layer.

The metal layer may be of any thickness that provides the desired encapsulation. The coating thickness is preferably as thin as possible, because implantable medical devices, such as stents, may be flexed significantly during deployment, and a very thin coating is less likely to affect the mechanical properties of the device or to be affected by the flexing. For example, the metal layer preferably is less than about 50,000 Å thick, more preferably less than about 10,000 Å thick.

An adhesion layer may be deposited onto the body before deposition of the istope. The adhesion layer comprises a material, preferably a metal, which improves adhesion of the isotope to the body. The adhesion layer preferably comprises at least one material selected from the group consisting of aluminum, silicon, titanium, vanadium, palladium, manganese, copper, nickel, gold, and rhodium. Preferred materials include titanium and gold. The adhesion layer may be deposited by any of a variety of well known coating methods, such as thermal boat evaporation, electron beam evaporation, sputtering, or another effusion cell. The adhesion layer may be deposited in a separate device from the isotope layer or the metal layer. The adhesion layer may be of any thickness that improves the adhesion of the isotope to the body, preferably as thin as possible to avoid altering the physical properties of the device. For example, the adhesion layer preferably is less than about 2000 Å thick, more preferably less than about 500 Å thick.

Another aspect of the present invention relates to apparatus for manufacturing medical devices such as described above. Such an apparatus comprises a source of a radioisotope or non-radioactive precursor isotope which provides a focused source of the isotope, such as an effusion cell, and a support for holding a medical device to be coated. Preferably, the support is movable to present different portions of the device to the isotope source. The device may further comprise a source for a metal coating. This source may be capable of depositing a coating of metal onto the device either during or after deposition of the isotope.

In the apparatus, the implantable medical device preferably is movable relative to the narrow stream of coating material in order to uniformly coat the desired surface area of the device. Exemplary motions may include either or both rotation and linear translation, depending on the shape of the implantable medical device. The flux of the radioactive isotope or non-radioactive isotope may not necessarily impinge on the medical device body at precisely the same time or location as the metal coating, but it is desired that a selected ratio between the deposition rate of each type of flux should be maintained to effect encapsulation.

DETAILED DESCRIPTION OF THE PREFERRED EMBODIMENTS

Many medical devices are made from metals such as titanium alloy, nitinol (NiTi), or stainless steel. FIG. 1 shows an example of such a device, called a stent, which is used for maintaining the patency of coronary arteries. The stent is an example of an implantable medical device whose efficacy can be usefully improved by the addition of a radioactive isotope.

Radioactive isotopes are inherently hazardous and costly. Therefore, it is important to utilize radioactive isotopes as efficiently as possible in order to minimize resultant radioactive waste, the cost of materials, and the hazards associated with handling them. It is preferred that processes that add radioactive isotopes to implantable medical devices utilize and transfer the radioactive isotopes to the implantable medical devices as efficiently as possible. While many such processes are known to exist, each tends to be specialized for working with only one or a limited range of elements. A useful, somewhat more general method is to use vapor deposition to deposit a coating.

The present method comprises a high-efficiency vapor desposition method utilizing an effusion cell to apply the precursor isotope or radioisotope. The term 'effusion cell' refers to a cell or furnace for creating a vapor from a source which can then be deposited on a substrate. The method comprises heating a radioactive isotope in an effusion cell under conditions sufficient to vaporize atoms of the isotope, and disposing a layer of the atoms of the isotope on a body. The method may further comprise disposing a layer of metal onto the body. The metal coating may be deposited subsequent to or substantially simultaneously with disposing a layer of the isotope on the body. The method may further comprise disposing an adhesion layer onto the body prior to disposing the later of the isotope on the body.

The effusion cell was originally devised by Knudsen as a research tool for the precision measurement of vapor pressure. See for example "Handbook of Thin Film Technology", Leon I Maissel and Reinhard Glang, McGraw-Hill Book Company, New York, 1970, pp. 1–26 to 1–28. The effusion cell is usually characterized by a low evaporant flux output spread over a relatively small area. Most high-throughput industrial coating processes require a much greater evaporant flux for cost efficiency, and thus the effusion cell is normally employed solely for high precision, non-radioactive coating applications, as are common in semiconductor research using molecular beam epitaxy equipment.

Figure 2:
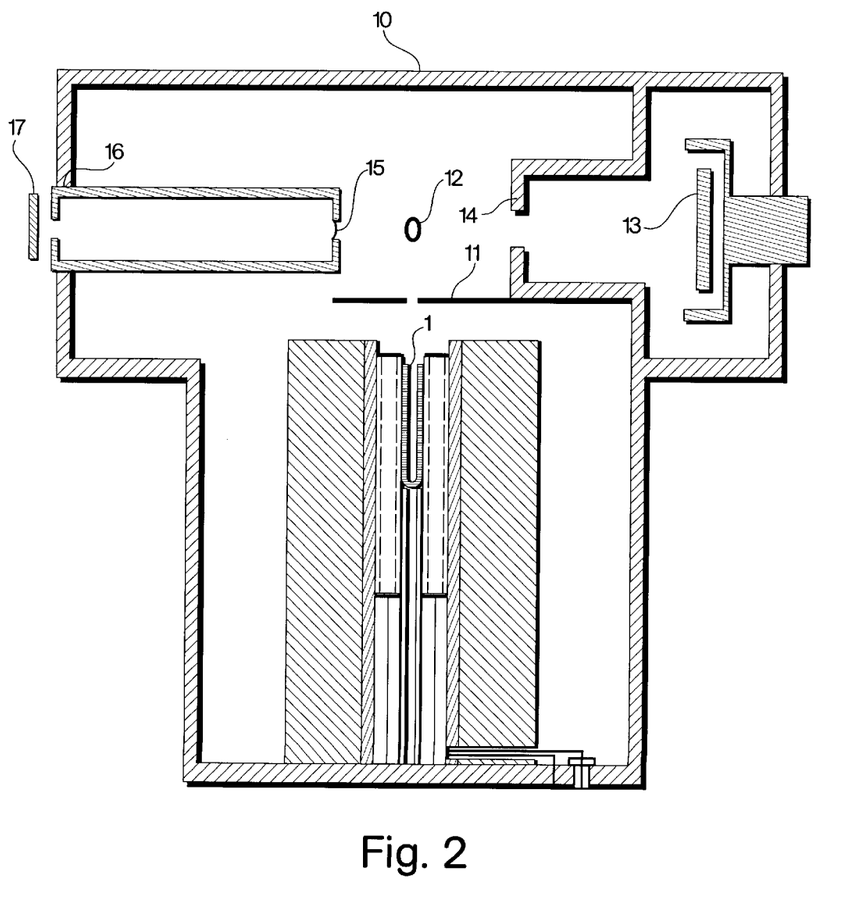
FIG. 2 illustrates an effusion cell for a radioactive isotope.

The effusion cell comprises an enclosed, thermnally heated volume which possesses a small diameter orifice for vapors to be emitted. The orifice is preferably less than about 3 mm in diameter and preferably about 1–1.5 mm in diameter. A narrow, conically expanding jet of vapor emanates from the orifice. FIG. 2 shows a diagram of a typical effusion cell 1. The cell has an electrical resistance heating element 2, thermal insulation 3, and orifice 4. The enclosed heated volume is used to hold the radioactive isotope 5 to be evaporated.

In the method of the invention, the temperature of the effusion cell may be controlled to modify or maintain the production rate of radioactive vapor. Additionally, other factors, such as the size of the remaining vapor-emitting particles of radioactive isotope material, may also affect the production rate of radioactive vapor. For this reason, is important to independently measure the accumulated intensity of radioactive nuclear radiation coming from the medical device while it is being coated in order to establish when the coating has become sufficiently thick and the nuclear radiation has become sufficiently intense.

The present method comprises the use of an effusion cell specifically for the application of a radioactive or precursor isotope to a medical device resulting in a high utilization efficiency of the evaporant over a small coating area. Conventional evaporation devices, such as electron beam evaporators or thermal boat evaporators, evaporate atoms into approximately a $2\pi$ solid angle (a hemisphere). Most of the radioactive material thus would be wastefully lost on walls of the vacuum chamber or on shields, since the devices to be coated may occupy only a small portion of this hemispherical zone. The effusion cell can emit coating material into approximately a $0.02\pi$ solid angle and thus is far more efficient for coating small devices, aiming as much as about 10–50% of the evaporated radioactive material directly onto the small implantable medical device, rather than wastefully onto shields or walls.

This efficiency is critical because the cost of radioactive isotopes is very high. Additionally, some radioactive isotopes of importance, such as $^{103}Pd$, are most easily fabricated from an isotopically enriched non-radioactive precursor, such as $^{102}Pd$, and this costly precursor feedstock is only available in milligram quantities. Coating many devices with a small quantity of radioactive material can be accomplished using a process having very high feedstock utilization efficiency.

An additional advantage of the present process utilizing an effusion cell is that the waste-coated radioactive material can be easily collected because the surface area of the shields used for collection can be kept very small. The waste radioactive material and the shield on which it has been deposited can be placed within the effusion furnace and re-evaporated multiple times, effectively recycling the waste material, thus further increasing utilization efficiency to near 100%. A shield may be fabricated from any convenient refractory material. In a preferred embodiment, the shield is made from thin, e.g., about 0.001 inch thick, tantalum, which has a very low vapor pressure at the evaporation temperatures of interest for medically useful radioactive isotopes, and thus does not substantially contribute to the evaporated coating from the effusion furnace.

For small implantable medical devices, such as stents, it is preferable to position the device as close to the orifice of the effusion cell as possible for minimum dispersion of the jet. This distance is preferably between about 1–2 cm for a stent. It is also preferable to provide a group of shields that can serve to collect and accumulate any radioactive isotope coating that may miss being deposited onto the surface of the implantable medical device. The shields are preferably fabricated from a thin foil made from a refractory material. A biocompatible material, such as tantalum or titanium, is preferred. The foil thickness is preferably as thin as possible, typically about 0.001 inches in thickness, so that the foil is easily flexible and bendable. The area of the foil shields is preferably as small as possible in order to facilitate bending the foil, together with any accumulated coating of radioactive isotopes, and placing the foil within the heated volume of the effusion furnace. The refractory material of the heated foil preferably should have a vapor pressure at least about 2 orders of magnitude less than that of the radioactive isotope at the same temperature so that the radioactive isotope can be substantially the only species being emitted by the effusion furnace.

Figure 3:
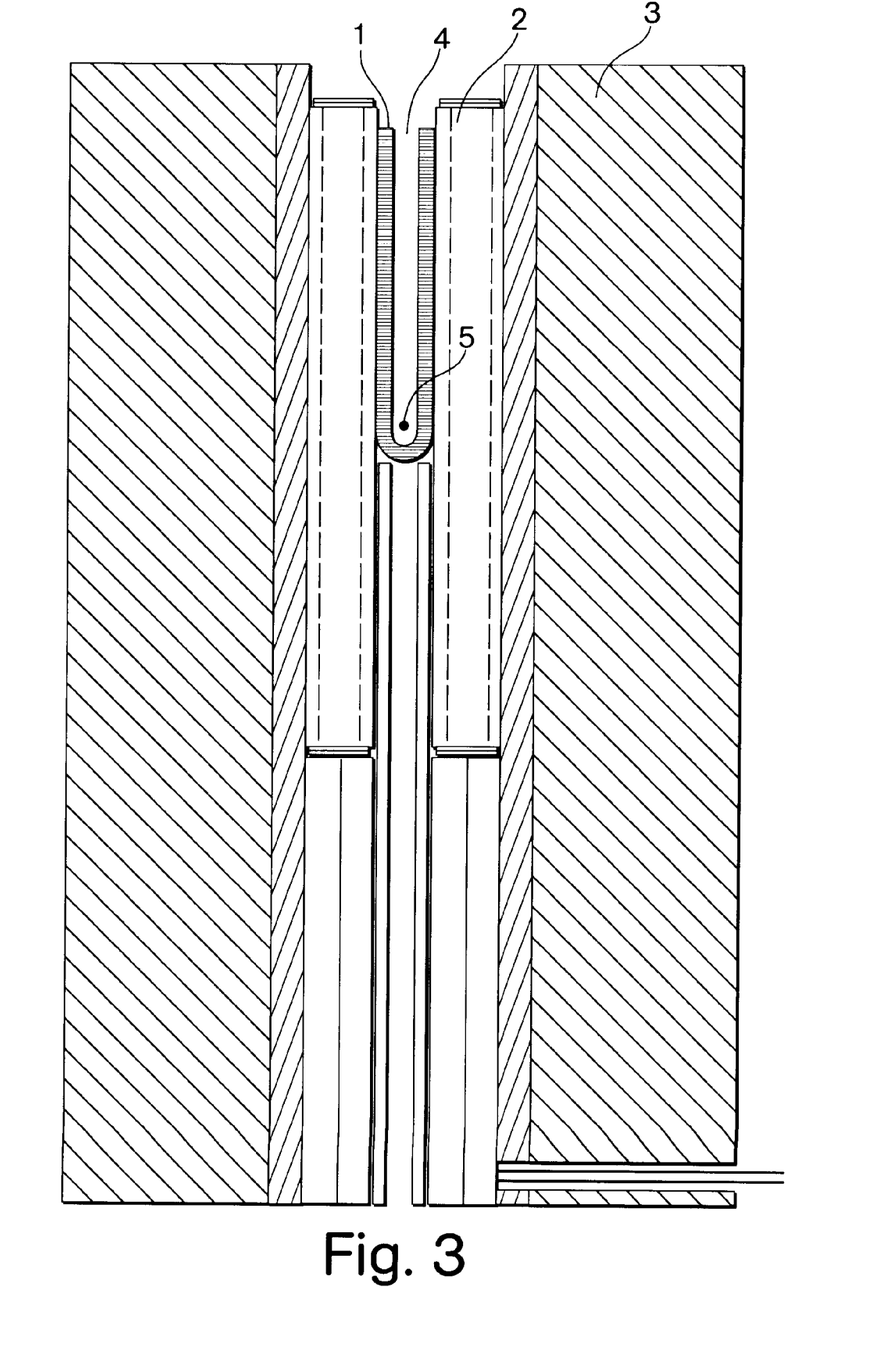
FIG. 3 illustrates coating a stent using an effusion cell together with a metal sputtering gun.

FIG. 3 illustrates a vacuum chamber 10 containing an effusion cell 1 for depositing the radioactive isotope coating, refractory material shields 11, a stent 12 to be coated with either or both a radioactive isotope material and a metal, and a sputtering gun 13 for depositing a metal coating. The sputtering gun 13 may be operated either simultaneously with the effusion cell 1 or sequentially with the sputtering gun providing an overcoat after the radioactive isotope coating has been deposited. In some embodiments, it may be desirable to coat only specific surfaces of the stent 12 or other implantable medical device. Therefore, it is preferred that a system for manipulating the orientation of the stent 12 be supplied in order to present all of the desired surfaces to the jet of radioactive vapor from the effusion cell 1 and the sputtering gun 13.

The sputtering gun 13 is one method for applying an encapsulating metal coating. Other methods which may be employed include, for example, thermal boat evaporation, electron gun evaporation, or a separate, non-radioactive effusion furnace. The cost of the metal encapsulant typically is not nearly as great as for the radioactive isotope, and thus less efficient coating methods may be usefully employed for convenience. Furthermore, because the material is not radioactive, material lost on the walls of the apparatus does not present a hazard. It is preferred that a separate set of shields 14 be used to restrict the path of the flux of vapor from the sputtering gun 13 in order to better control the metal coating deposition rate relative to that of the radioactive isotope coating from the effusion furnace 1. While the precise relative coating rates depend on the specific materials being employed, it is preferred that the metal coating deposition rate be between about 1 and about 10 times that of the radioactive isotope coating deposition rate.

The deposition rate of the effusion cell 1 is preferably controlled by varying the temperature. The deposition rate of the sputtering gun 13 or its equivalent method is preferably controlled using means typical of the selected coating method. For example, the sputtering gun 13 deposition rate is controlled by the applied power or by the distance between the sputtering gun and the stent 12. Additionally, finer control may be achieved preferably by means of a variable mechanical shutter.

It is preferred that the radioactive radiation being emitted by the accumulated radioactive isotope coating be measured while the radioactive isotope coating is being deposited. FIG. 3 illustrates a thin window 15 in the vacuum chamber 10 through which the nuclear radiation can substantially pass. While such a window can be fabricated from a variety of materials and thicknesses depending on the type of nuclear radiation being emitted by the radioactive isotope coating, a useful vacuum window for most cases could be fabricated of about 0.001 inch thick mylar. A collimator 16 is used to permit the nuclear radiation detector 17 to view a limited region on the surface of the stent 12. The collimator 16 is preferred in order to minimize the viewing of radioactive isotope coating that may be located on a shield 11, rather than a stent 12. The measurement of the nuclear radiation using detector 17 may preferably be used to determine when the desired thickness of radioactive isotope coating has been accomplished.

A radioactive medical device manufactured by the process described above comprises a body having a layer of a radioisotope or non-radioactive precursor isotope disposed thereon. Exemplary precursor isotopes which can be activated by exposure to a source of thermal neutrons include, for example, ytterbium-168, barium-130, phosphorus-31, palladium-102, yttrium-89, rhenium-185, and rhenium-187. Preferred radioisotopes comprise, for example, phosphorus-32, iodine-125, palladium-103, yttrium-90, cesium-131, and ytterbium-169. Mixtures or combinations of more than one precursor or radioactive isotope may be used. In preferred embodiments, the layer of radioisotope or non-radioactive precursor isotope is less than about 250 Å thick, even more preferably between about 50 Å and about 100 Å.

A radioactive medical device may further comprise an adhesion layer. The adhesion layer comprises a material which improves adhesion of the isotope to the body. The adhesion layer preferably comprises at least one material selected from the group consisting of aluminum, silicon, titanium, vanadium, palladium, manganese, copper, nickel, gold, and rhodium. Preferred materials include titanium and gold. The adhesion layer may be of any thickness that improves the adhesion of the isotope to the body, preferably as thin as possible to avoid altering the physical properties of the device. For example, the adhesion layer preferably is less than about 2000 Å thick, more preferably less than about 500 Å thick.

The device may further comprise a layer of metal to encapsulate the radioactive isotope. Examples of suitable metals comprise, but are not limited to, titanium, gold, tantalum, carbon, titanium-aluminum-vanadium alloy, stainless steel, cobalt-chrome alloy, cobalt-chrome-molybdenum alloy, rhodium, lead, copper, platinum, and palladium. Preferred materials comprise titanium, gold, tantalum, titanium alloy, stainless steel, cobalt-chrome alloy, platinum, and palladium. The metal layer preferably is less than about 50,000 Å thick, more preferably less than about 10,000 Å thick.

In a preferred embodiment for manufacturing a radioactive medical device, an adhesion layer is first disposed on a body. The adhesion coating may be of any material set forth above, preferably titanium or gold, and is preferably less than about 500 Å thick. The adhesion coating may be disposed on the body by any means set forth above, either in an apparatus having an effusion cell or in any other apparatus.

The radioactive or non-radioactive isotope then is deposited on the adhesion layer, preferably using an effusion cell. The isotope may be any of the radioactive or non-radioactive isotopes set forth above, preferably phosphorus-32, palladium-103, yttrium-90, cesium-131, or ytterbium-169. In preferred embodiments, an even coating of the isotope may be achieved by moving the body with respect to the effusion cell to present all surfaces of the body to the flux of atoms of the isotope. In a preferred embodiment, an encapsulating metal layer is deposited substantially simultaneously with the isotope to maximize the retention of atoms of the isotope. The metal layer may be deposited by any technique set forth above, preferably by sputtering. The metal layer may comprise any metal described above, preferably titanium, gold, or a titanium alloy. When the isotope is a radioisotope, the amount of the isotope deposited may preferably be controlled by monitoring the radioactivity of the device during deposition of the radioactive isotope. If the isotope is deposited prior to deposition of the metal layer, the layer of the isotope is preferably less than about 250 Å. The metal layer is preferably less than about 50,000 Å thick.

If a non-radioactive isotope is used in the above procedure, the body comprising the non-radioactive isotope is preferably exposed to a source of thermal neutrons under conditions sufficient to generate a radioisotope. If the isotope is deposited separately from the metal layer, the non-radioactive isotope may be activated before or after the metal layer is disposed on the body.

The following examples further illustrate the invention, and are not intended to be limiting in any way.

EXAMPLE 1

This example illustrates the procedure used to coat a stainless steel coronary stent of approximately 18 mm in length and 2 mm in diameter. The stent first was coated with an adhesion coating comprising 2000 Å of pure titanium using magnetron sputtering in a non-radioactive apparatus separate from the apparatus containing a radioactive effusion cell. The stent coated with the adhesion coating then was transferred to a vacuum system containing an effusion cell.

The effusion cell was loaded with about 0.003 grams of radioactive palladium metal powder. A sputter gun with a pure titanium cathode was used for depositing the metal coating. The vacuum chamber was evacuated to a pressure less than about $1 \times 10^{-5}$ Torr. The effusion cell was heated to 1250° C. The 18 mm long stent was both rotated and linearly translated while being coated for approximately 2 hours. The sputter gun was simultaneously operated at 4 millitorr and 150 Watts. A NaI(T1) nuclear radiation detector was used to determine the end of the radioactive isotope coating period, when the count rate for palladium x-rays around 20 keV reached 150 counts per second. The effusion cell was turned off, and the sputter gun continued to operate for another 15 minutes to ensure that the radioactive isotopes were fully embedded in titanium.

EXAMPLE 2

The following procedure describes a process for making a high activity radioactive wire used for temporary intravascular brachytherapy by ion-implanting a non-radioactive precursor.

A copper wire of 99.999% purity and 0.008" in diameter was simultaneously ion-implanted with $^{168}$Yb using a mass-analyzed ion implanter and simultaneously coated with copper evaporated from an electron beam evaporator. This procedure effectively encapsulates the $^{168}$Yb atoms within the copper coating and also compensates for the sputter loss from the wire by the high energy ion beam. This procedure is similar to that used to ion-implant a zirconia coating, as described more fully in U.S. Pat. No. 5,383,934 to A. J. Armini and S. N. Bunker, assigned to the common assignee.

The $^{168}$Yb ion beam had a current density of 0.3 $\mu$A/cm$^2$ at a kinetic energy of 60 keV. In 14.8 hours, $3 \times 10^{15}$ atoms of $^{168}$Yb per centimeter of wire length were embedded in the wire. The copper evaporation rate was 0.5 $\mu$Å/s, depositing a coating approximately 2.6 microns thick.

The wire was then placed in the Oak Ridge high flux isotope reactor at a thermal flux of $2 \times 10^{15}$ neutrons/cm$^2$s for two weeks. After a 10-day cooling period, the 12-hour half-life radioisotopes produced from the copper were essentially gone and the wire emitted 126 mCi/cm length of pure $^{169}$Yb radiation. Six or more wires of this strength are sufficient to perform intravascular brachytherapy after angioplasty.

Equivalents

While the invention has been disclosed in connection with the preferred embodiments shown and described in detail, various equivalents, modifications, and improvements will be apparent to one of ordinary skill in the art from the above description. Such equivalents, modifications, and improvements are intended to be encompassed by the following claims.

What is claimed is:

1. A method for manufacturing a radioactive medical device, comprising heating a radioactive isotope in an effusion cell under conditions sufficient to vaporize atoms of the isotope; and disposing a layer of the atoms of the isotope on a body.

2. The method of claim 1, wherein the layer of atoms disposed on the body is less than about 250 Å thick.

3. The method of claim 1, wherein the radioactive isotope is selected from the group consisting of $^{32}P$, $^{90}Y$, $^{103}Pd$, $^{125}I$, $^{131}Cs$, and $^{169}Yb$.

4. The method of claim 1, wherein the intensity of radioactivity of the atoms disposed on the body is measured using a nuclear radiation detector substantially simultaneously to disposing the layer of the atoms on the body.

5. The method of claim 1, further comprising disposing an adhesion layer onto the body prior to disposing the layer of the atoms of the isotope on the body.

6. The method of claim 1, further comprising disposing a metal layer onto the body.

7. The method of claim 6, wherein disposing the metal layer occurs substantially simultaneously with depositing the layer of the atoms onto the body.

8. The method of claim 6, wherein disposing the metal layer is performed by a method selected from the group consisting of thermal boat evaporation, electron beam evaporation, sputtering, and a second effusion cell.

9. The method of claim 6, wherein said metal layer comprises a biocompatible material including one or more materials from the group consisting of titanium, titanium alloy, gold, copper, tantalum, stainless steel, cobalt-chrome alloy, platinum, and palladium.

10. The method of claim 6, further comprising disposing an adhesion layer onto the body prior to disposing the layer of the atoms of the isotope on the body.

11. The method of claim 6, wherein the metal layer encapsulates the radioactive isotope.

12. A method for manufacturing a medical device, comprising heating a non-radioactive precursor isotope in an effusion cell under conditions sufficient to vaporize atoms of the isotope; and disposing a layer of the atoms of the isotope on a body.

13. The method of claim 12, wherein the layer of atoms disposed on the body is less than about 250 Å thick.

14. The method of claim 12, wherein the non-radioactive precursor isotope is selected from the group consisting of $^{31}P$, $^{89}Y$, $^{102}Pd$, $^{185}Re$, $^{187}Re$, $^{130}Ba$, and $^{168}Yb$.

15. The method of claim 12, further comprising exposing the body having the layer of atoms disposed thereon to a source of thermal neutrons under conditions sufficient to activate the atoms of the isotope.

16. The method of claim 12, further comprising disposing an adhesion layer onto the body prior to disposing the layer of the atoms of the isotope on the body.

17. The method of claim 12, further comprising disposing a metal layer onto the body.

18. The method of claim 17, wherein disposing a metal layer occurs substantially simultaneously with disposing the layer of the atoms onto the body.

19. The method of claim 17, wherein said metal layer comprises one or more materials selected from the group consisting of titanium, titanium alloy, gold, copper, tantalum, stainless steel, cobalt-chrome alloy, platinum, and palladium.

20. The method of claim 17, wherein disposing a metal layer is performed by a method selected from the group consisting of thermal boat evaporation, electron beam evaporation, sputtering, and a second effusion cell.

21. The method of claim 17, wherein the metal layer does not comprise a material which neutron activates to long-lived radioisotopes.

22. The method of claim 17, wherein the metal layer encapsulates the non-radioactive precursor isotope.

23. A medical device manufactured by heating a non-radioactive precursor isotope in an effusion cell under conditions sufficient to vaporize atoms of the isotope; and disposing a layer of the atoms of the isotope on a body.

24. The medical device of claim 23, which is rendered radioactive by exposing the device to a source of thermal neutrons under conditions sufficient to activate the precursor isotope.

25. A radioactive medical device manufactured by heating a radioactive isotope in an effusion cell under conditions sufficient to vaporize atoms of the isotope; and disposing a layer of the atoms of the isotope on a body.

* * * * *

UNITED STATES PATENT AND TRADEMARK OFFICE
CERTIFICATE OF CORRECTION

PATENT NO. : 6,059,714

DATED : May 9, 2000

INVENTOR(S) : Anthony J. Armini; Stephen N. Bunker

It is certified that error appears in the above-identified patent and that said Letters Patent is hereby corrected as shown below:

In column 6, please delete lines 1-3 and insert therefor

--FIG. 2 illustrates coating a stent using an effusion cell together with a metal sputtering gun.

FIG. 3 illustrates an effusion cell for a radioactive isotope.--

In column 6, line 59, delete "FIG. 2" and insert therefor --FIG. 3--.

In column 8, line 3, delete "FIG. 3" and insert therefor --FIG. 2--.

In column 8, line 49, delete "FIG. 3" and insert therefor --FIG. 2--.

Signed and Sealed this

Twenty-seventh Day of March, 2001

NICHOLAS P. GODICI

*Attest:*

*Attesting Officer*  Acting Director of the United States Patent and Trademark Office